United States Patent
Graessle et al.

(10) Patent No.: US 7,715,895 B1
(45) Date of Patent: May 11, 2010

(54) SEPARATE LOCAL RF TRANSMIT AND RECEIVE COILS FOR BREAST MRI SYSTEM

(75) Inventors: David Graessle, Dublin, OH (US); Mathew A. Hass, Andover, MA (US)

(73) Assignee: Aurora Imaging Technology, Inc., North Andover, MA (US)

( * ) Notice: Subject to any disclaimer, the term of this patent is extended or adjusted under 35 U.S.C. 154(b) by 149 days.

(21) Appl. No.: 10/302,767

(22) Filed: Nov. 21, 2002

Related U.S. Application Data

(60) Provisional application No. 60/332,628, filed on Nov. 21, 2001.

(51) Int. Cl.
*A61B 5/05* (2006.01)

(52) U.S. Cl. ............... 600/407; 600/408; 600/409; 600/410; 324/306; 324/307; 324/309; 324/318; 324/322

(58) Field of Classification Search ......... 600/407–423; 324/318, 322
See application file for complete search history.

(56) References Cited

U.S. PATENT DOCUMENTS

| | | | |
|---|---|---|---|
| 5,078,142 A | 1/1992 | Siczek et al. | |
| 5,289,520 A | 2/1994 | Pellegrino et al. | |
| 5,363,845 A * | 11/1994 | Chowdhury et al. | 600/422 |
| 5,386,447 A | 1/1995 | Siczek | |
| 5,409,497 A | 4/1995 | Siczek et al. | |
| 5,534,778 A | 7/1996 | Loos et al. | |
| 5,569,266 A | 10/1996 | Siczek | |
| 5,590,655 A | 1/1997 | Hussman | |
| 5,678,549 A | 10/1997 | Heywang-Koebrunner et al. | |
| 5,706,812 A | 1/1998 | Strenk et al. | |
| 5,804,969 A * | 9/1998 | Lian et al. | 324/318 |
| 5,855,554 A | 1/1999 | Schneider et al. | |

(Continued)

FOREIGN PATENT DOCUMENTS

DE 19626286 1/1998

OTHER PUBLICATIONS deSouza et al., "MR-Guided Biopsy of the Breast After Lumpectomy and Radiation Therapy Using Two Methods of Immobilization in the Lateral Decubitus Position," JMRI, pp. 525-528 (Sep./Oct. 1995).

(Continued)

*Primary Examiner*—Brian Casler
*Assistant Examiner*—John F Ramirez
(74) *Attorney, Agent, or Firm*—Fish & Richardson P.C.

(57) ABSTRACT

A magnetic resonance imaging system for imaging human breasts, in which the system includes a main magnet providing a static magnetic field, a gradient coil insert received within the internal bore of the main magnet, the gradient coil insert including gradient coils providing a spatially varying magnetic field, a patient support table configured to support the patient within the patient opening, the patient support table including a patient support member with at least one breast opening sized and positioned so that in use the patient's breast extends through the opening and is accessible below the patient support member, an RF transmitter coil mounted on the patient support table in the vicinity of the at least one breast opening, and an RF receiver coil separate from the RF transmitter coil and mounted on the patient support table in the vicinity of the at least one breast opening.

7 Claims, 4 Drawing Sheets

U.S. PATENT DOCUMENTS

| | | | |
|---|---|---|---|
| 5,913,863 A | | 6/1999 | Fischer et al. |
| 6,023,166 A | * | 2/2000 | Eydelman .................. 324/318 |
| 6,163,717 A | * | 12/2000 | Su ............................ 600/422 |
| 6,254,538 B1 | | 7/2001 | Downey et al. |
| 6,423,076 B1 | | 7/2002 | Cardwell et al. |
| 6,701,178 B2 | * | 3/2004 | Su et al. .................... 600/422 |
| 6,850,065 B1 | * | 2/2005 | Fujita et al. ................ 324/318 |
| 2002/0156365 A1 | | 10/2002 | Tsekos |
| 2003/0007598 A1 | | 1/2003 | Wang et al. |

OTHER PUBLICATIONS

Doler et al., "Stereotaxic Add-on Device for MR-guided Biopsy of Breast Lesions," pp. 863-864 (Sep. 1996).

Fischer et al., "Magnetic Resonance Guidance Localization and Biopsy of Suspicious Breast Lesions," Topics in Magnetic Resonance Imaging, 9(1):44-59 (1998).

Heywang-Kobrunner et al., "MR-Guided Percutaneous Vaccum Assisted Biopsy of Enhancing Breast Lesions," Electromedica, 67(2):67-45 (1999).

Heywang-Kobrunner et al., "Prototype Breast Coil for MR-Guided Needle Localization," Journal of Computer Assisted Tomography, 18(6):876-881 (1994).

Hussman et al., "MR Mammographic Localization—Work in Progress," Radiology, 189(3):915-917 (1993).

Schnall et al., "MR Guided Biopsy of the Breast," Breast Imaging, MRI Clinics of North America, 2(4):585-589 (Nov. 1994).

* cited by examiner

SEPARATE LOCAL RF TRANSMIT AND RECEIVE COILS FOR BREAST MRI SYSTEM

CROSS-REFERENCE TO RELATED APPLICATIONS

This application claims priority to U.S. Provisional Application Ser. No. 60/332,628, filed on Nov. 21, 2001 (hereby incorporated by reference). This application incorporates by reference the disclosure of U.S. patent application entitled "Patient Support Table for Breast MRI System", filed on even date herewith.

BACKGROUND

The invention relates to magnetic resonance imaging (MRI) systems, particularly MRI systems for imaging breasts.

MRI systems typically employ a main magnet that produces a static magnetic field and gradient coils that superimpose spatially varying magnetic fields on top of the static field. The gradient coils are typically formed on a cylindrical insert that fits within the bore of the main magnet. Inside of the gradient coil insert there is usually a whole-body RF transmitting coil, which often also serves as the RF receiving coil. The RF transmitting coil excites the molecules of the anatomy being imaged, and the RF receiving coil detects the response of the molecules.

Sometimes, a separate RF receiving coil is positioned locally in the vicinity of the anatomy being imaged, e.g., around a breast. One prior art system (manufactured by Caprius) used a combined transmitting/receiving RF coil localized around a breast.

SUMMARY

We have discovered that it is advantageous in breast MRI to use separate localized transmitter and receiver RF coils. Removing the RF transmitting coil from its conventional location just inside the gradient coil insert increases the interior space within the MRI bore. Moving the RF transmitter coil away from that conventional location has the disadvantage that the uniform overall RF field is lost, but it turns out to be possible to generate a uniform RF field in the vicinity of the breasts. The smaller volume over which the RF field must be produced reduces the electrical power consumption. Having the receive RF coil close to the breasts increase the accuracy of the imaging by reducing the magnitude of extraneous signals picked up by the receive coil.

In general, the invention features a magnetic resonance imaging system for imaging human breasts, in which the system comprises a main magnet providing a static magnetic field, a gradient coil insert received within the internal bore of the main magnet, the gradient coil insert comprising gradient coils providing a spatially varying magnetic field, a patient support table configured to support the patient within the patient opening, the patient support table comprising a patient support member with at least one breast opening sized and positioned so that in use the patient's breast extends through the opening and is accessible below the patient support member, an RF transmitter coil mounted on the patient support table in the vicinity of the at least one breast opening, and an RF receiver coil separate from the RF transmitter coil and mounted on the patient support table in the vicinity of the at least one breast opening.

Preferred implementations of the invention may incorporate one or more of the following features: The RF transmit coil may be further away from the breast opening than the RF receive coil. The RF transmit coil may radially surrounds the RF receive coil. The RF transmit coil may comprise a loop element and a saddle element. The saddle element may provide an X directed field and the loop element provides a Y directed field. The RF receive coil may comprise a loop element and a saddle element.

Other features and advantages of the invention will be apparent from the following detailed description and drawings, and from the claims.

DETAILED DESCRIPTION

Descriptions of the breast MRI system in which the invention is used can be found in the application attached in the Appendix hereto. The application includes details as to the construction of the patient support table.

The RF transmit and receive coils are constructed within molded shells 200, 202 which are fastened to the undersurface of the chest support member. The shells are not structural, and serve only to support the RF coils, and screen them from view. Once installed, the coils are complete hidden inside the shells, which are made from the same molded material as the chest support member. The receive shell 202 fits laterally within the transmit shell 200.

Figure 3:
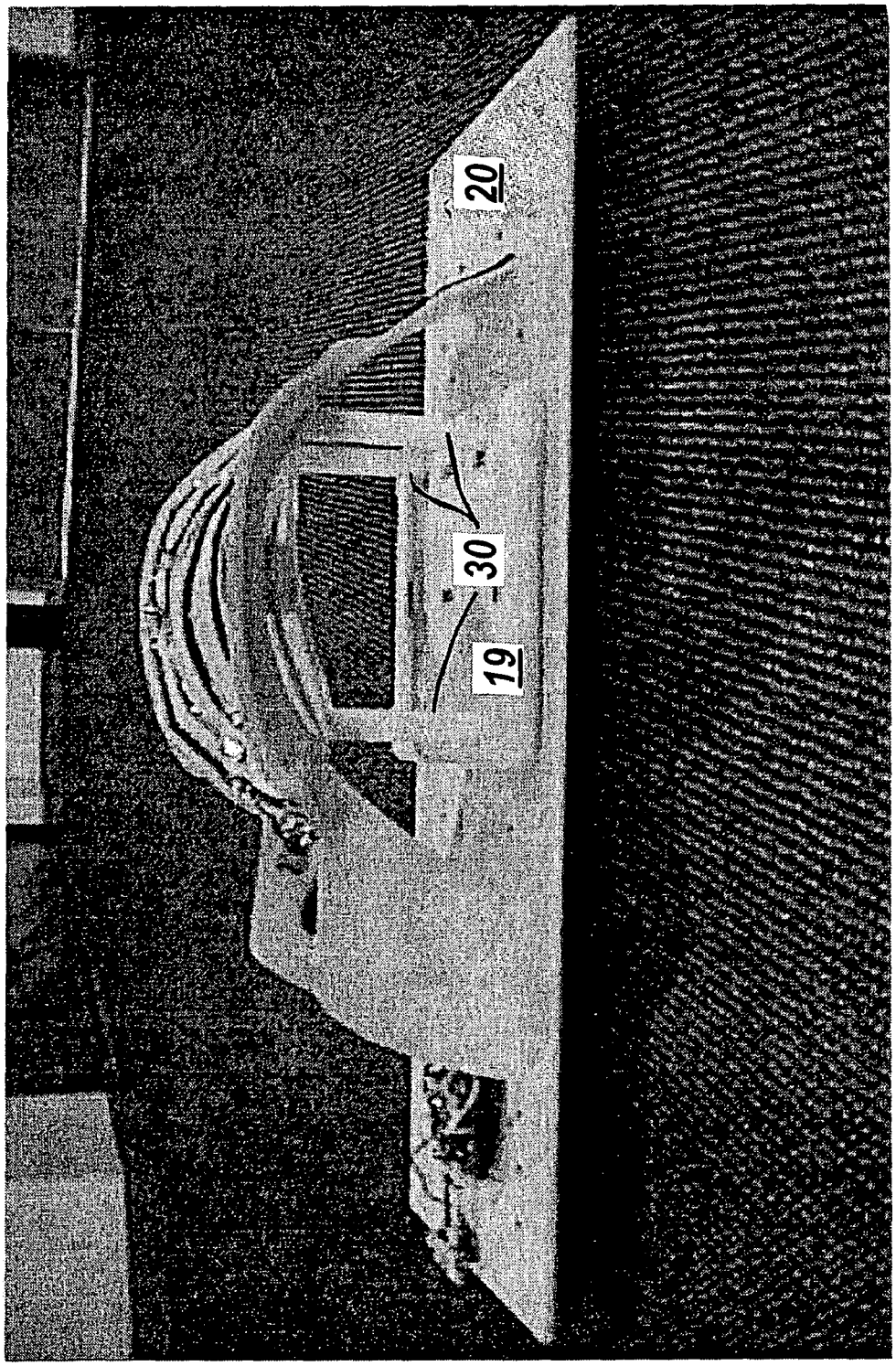
FIGS. 3-4 are perspective views (photographs) of the RF coil insert that is secured to the undersurface of the chest support member of the patient support table.
Figure 4:
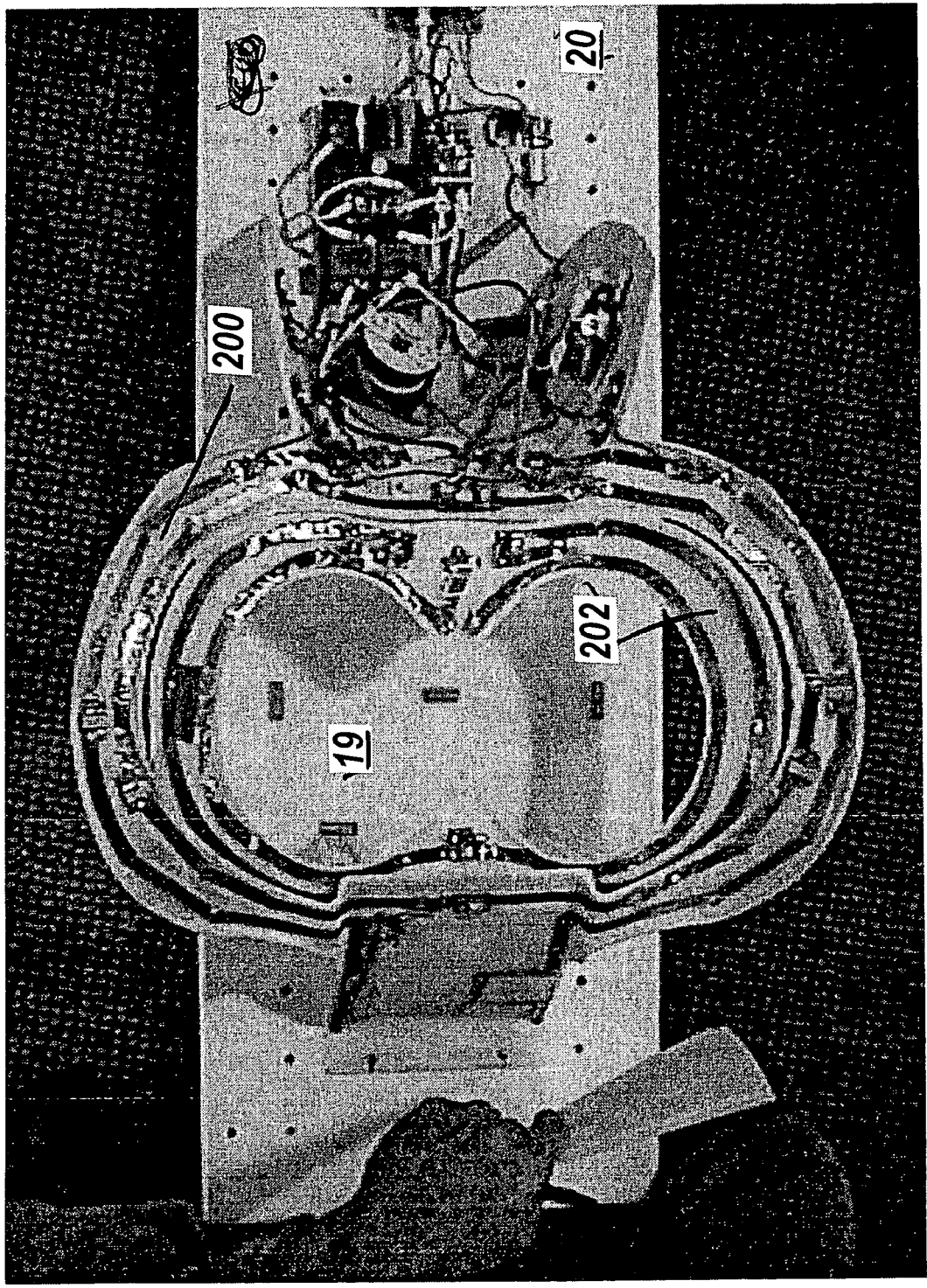

FIGS. 3 and 4 show prototype coils formed by soldering solid copper segments together. Manufactured products will have a copper plated flexible circuit in place of the soldered copper pieces.

Figure 1:
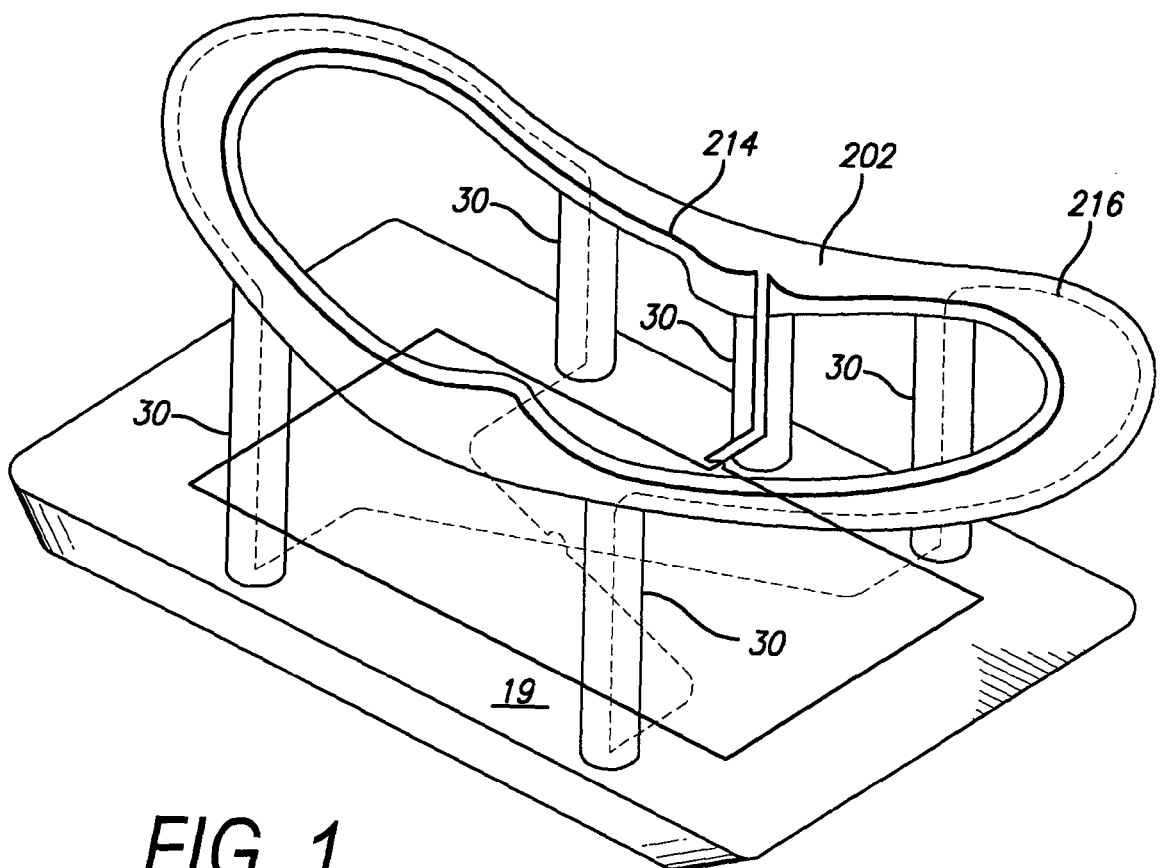
FIG. 1 is a diagrammatic perspective view of the layout of the conductors making up the RF receive coils.
Figure 2:
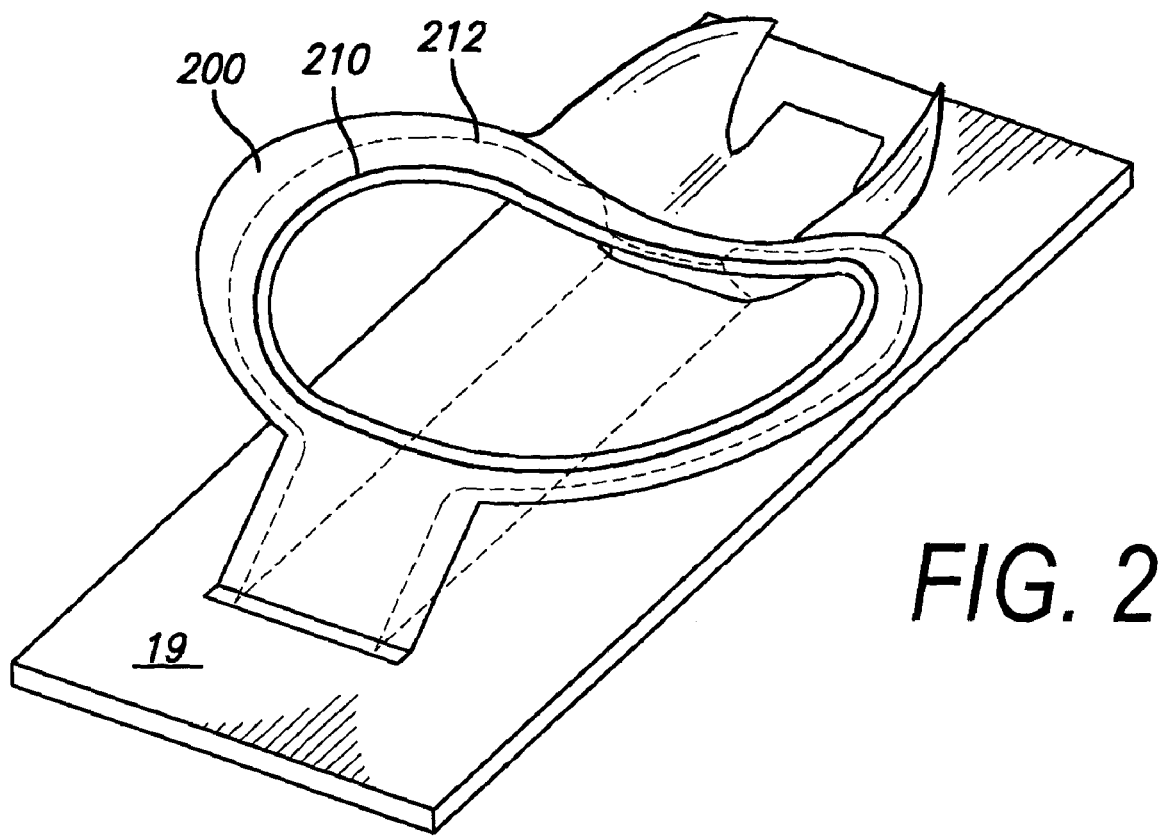
FIG. 2 is a diagrammatic perspective view of the layout of the conductors making up the RF transmitter coils.

The transmit coil is shown diagrammatically in FIG. 2. It is laterally (radially) outside of the receive coil, where it is further away from the breasts of the patient. This is preferable to its being at the same distance from the receive coils, or to the same coil serving as both the transmit and receive coil. The physics that govern the performance of RF coils show that greater uniformity in the field generated by the transmit coil can be had by moving the coil further away from the anatomy being excited. Even greater uniformity could be achieved by moving the transmit coil to the interior surface of the gradient coil, i.e., making it a whole-body transmit coil. But this would decrease the size of the patient opening (and require a higher power coil, which would be somewhat more expensive to manufacture).

The transmit coil is made up of a loop element 210 and a saddle element 212. The saddle element 212 is shown in dashed lines, and the loop element 210 in solid lines. The loop element makes a single loop within the shell just below the chest support member. The saddle element makes two loops, one on the left side and one on the right side of the patient. The conductors cross over at one end (does not show up well in the figure) so that the current rotation direction is the same in both loops of the saddle element. The two loops of the saddle element generate a field with a predominantly X directed component, whereas the single loop of the loop element generates a field with a predominantly Y directed component.

The receive coil also has both a loop element 214 and a saddle element 216. In this case there are two loops in the loop element and two loops in the saddle element. The same notation is used in this drawing as in FIG. 2. The saddle element is shown in dashed lines, and the loop element in solid lines. The loop element does one loop around the shell just below the chest support member, and then goes down through a column 30 and does a second loop beneath base element 19. The loop elements are oriented so as to receive predominantly Y directed fields. The saddle element 216 makes two loops, each of which is half up on the shell and half down at the base element. The saddle elements are hence oriented so as to receive predominantly Y directed fields.

Other embodiments of the invention are within the following claims.

What is claimed is:

1. A magnetic resonance imaging method for imaging human breasts, the method comprising
    placing a patient within a magnetic resonance imaging system comprising
        a main magnet providing a static magnetic field;
        a gradient coil insert received within an internal bore of the main magnet, the gradient coil insert comprising gradient coils providing a spatially varying magnetic field;
        a patient support table configured to support the patient within the patient opening, the patient support table comprising a patient support member with a patient support surface on which the patient is supported and
    placing a breast of the patient so that the breast extends through a breast opening sized and positioned so that in use the patient's breast extends through the opening and is accessible below the patient support member;
    providing an RF transmitter coil mounted below the patient support surface in the vicinity of the breast opening,
    providing an RF receiver coil separate from the RF transmitter coil and mounted below the patient support surface in the vicinity of the breast opening,
        wherein the RF transmitter coil is configured to serve for RF transmitting, and the RF receiver coil is configured to serve for RF reception; and
    exciting molecules of the patient's breast by transmitting RF signals using the RF transmitter coil; and
    detecting the response of the molecules of the patient's breast by receiving RF signals using the RF receiver coil.

2. The method of claim 1 wherein the RF transmitter coil is further away from the breast opening than the RF receive coil.

3. The method of claim 2 wherein the RF transmitter coil radially surrounds the RF receive coil.

4. The method of claim 1 wherein the RF transmitter coil comprises a loop element and a saddle element.

5. The method of claim 4 wherein the saddle element provides an X directed field and the loop element provides a Y directed field.

6. The method of claim 1 wherein the RF receiver coil comprise a loop element and a saddle element.

7. The method of claim 1 wherein a second breast extends through a second breast opening, and the RF transmitter coil and the RF receive coil are located so as to be in the vicinity of the first and second breast openings.

* * * * *

UNITED STATES PATENT AND TRADEMARK OFFICE
CERTIFICATE OF CORRECTION

| | | |
|---|---|---|
| PATENT NO. | : 7,715,895 B2 | |
| APPLICATION NO. | : 10/302767 | |
| DATED | : May 11, 2010 | |
| INVENTOR(S) | : Graessle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 117 days.

Signed and Sealed this

Fifth Day of October, 2010

David J. Kappos
*Director of the United States Patent and Trademark Office*